(12) United States Patent
Edwards

(10) Patent No.: US 10,010,885 B2
(45) Date of Patent: Jul. 3, 2018

(54) REAGENT DISPENSERS, DISPENSING APPARATUS, AND METHODS

(71) Applicant: Siemens Healthcare Diagnostics Inc., Tarrytown, NY (US)

(72) Inventor: Mark Edwards, Armonk, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/905,631

(22) PCT Filed: Jul. 22, 2014

(86) PCT No.: PCT/US2014/047568
§ 371 (c)(1),
(2) Date: Jan. 15, 2016

(87) PCT Pub. No.: WO2015/013253
PCT Pub. Date: Jan. 29, 2015

(65) Prior Publication Data
US 2016/0144364 A1    May 26, 2016

Related U.S. Application Data

(60) Provisional application No. 61/881,069, filed on Sep. 23, 2013, provisional application No. 61/858,230, filed on Jul. 25, 2013.

(51) Int. Cl.
*G01N 35/10* (2006.01)
*B01L 3/00* (2006.01)
(Continued)

(52) U.S. Cl.
CPC ............ *B01L 3/523* (2013.01); *B01L 3/0203* (2013.01); *B01L 9/00* (2013.01); *G01N 33/5304* (2013.01); *G01N 35/1002* (2013.01); *B01L 2200/16* (2013.01); *B01L 2300/04* (2013.01); *B01L 2300/0861* (2013.01);
(Continued)

(58) Field of Classification Search
None
See application file for complete search history.

(56) References Cited

U.S. PATENT DOCUMENTS 4,146,156 A * 3/1979 Cassia ............... A47K 5/1208
141/330
4,862,932 A   9/1989 Feinstein et al.
(Continued)

FOREIGN PATENT DOCUMENTS

FR    2 765 686 A1    1/1999

OTHER PUBLICATIONS

Supplementary EP Search Report dated Jul. 18, 2016 of corresponding European Application No. 14829124.8, 4 Pages.
(Continued)

*Primary Examiner* — P. Kathryn Wright

(57) ABSTRACT

Disclosed is a reagent dispenser apparatus. The reagent dispenser apparatus has a reagent container having a dispense port operable to open and close to dispense reagent. Dispense port may include a valve operable to dispense reagent from a bottom of the reagent container. Reagent dispensing apparatus, immunoassay apparatus and methods of operating the reagent dispenser apparatus are provided, as are other aspects.

11 Claims, 11 Drawing Sheets

(51) Int. Cl.
   *B01L 3/02* (2006.01)
   *B01L 9/00* (2006.01)
   *G01N 33/53* (2006.01)
   *G01N 35/04* (2006.01)

(52) U.S. Cl.
   CPC . *B01L 2300/123* (2013.01); *B01L 2400/0481* (2013.01); *B01L 2400/06* (2013.01); *B01L 2400/0605* (2013.01); *B01L 2400/082* (2013.01); *G01N 35/1011* (2013.01); *G01N 2035/0443* (2013.01)

(56) References Cited

U.S. PATENT DOCUMENTS

| | | | |
|---|---|---|---|
| 5,947,167 A * | 9/1999 | Bogen | B01L 3/0293 141/1 |
| 6,193,933 B1 | 2/2001 | Sasaki et al. | |
| 2004/0197230 A1 | 10/2004 | Lemme et al. | |
| 2005/0035156 A1 | 2/2005 | Hersch et al. | |
| 2006/0147351 A1 | 7/2006 | Falb et al. | |
| 2007/0272710 A1 | 11/2007 | Bui | |
| 2008/0006333 A1 | 1/2008 | Partridge et al. | |
| 2012/0193376 A1* | 8/2012 | Evans | A47K 5/1215 222/207 |
| 2012/0241045 A1 | 9/2012 | Aouad | |

OTHER PUBLICATIONS

PCT International Search Report and Written Opinion dated Apr. 22, 2015 (8 Pages).

\* cited by examiner

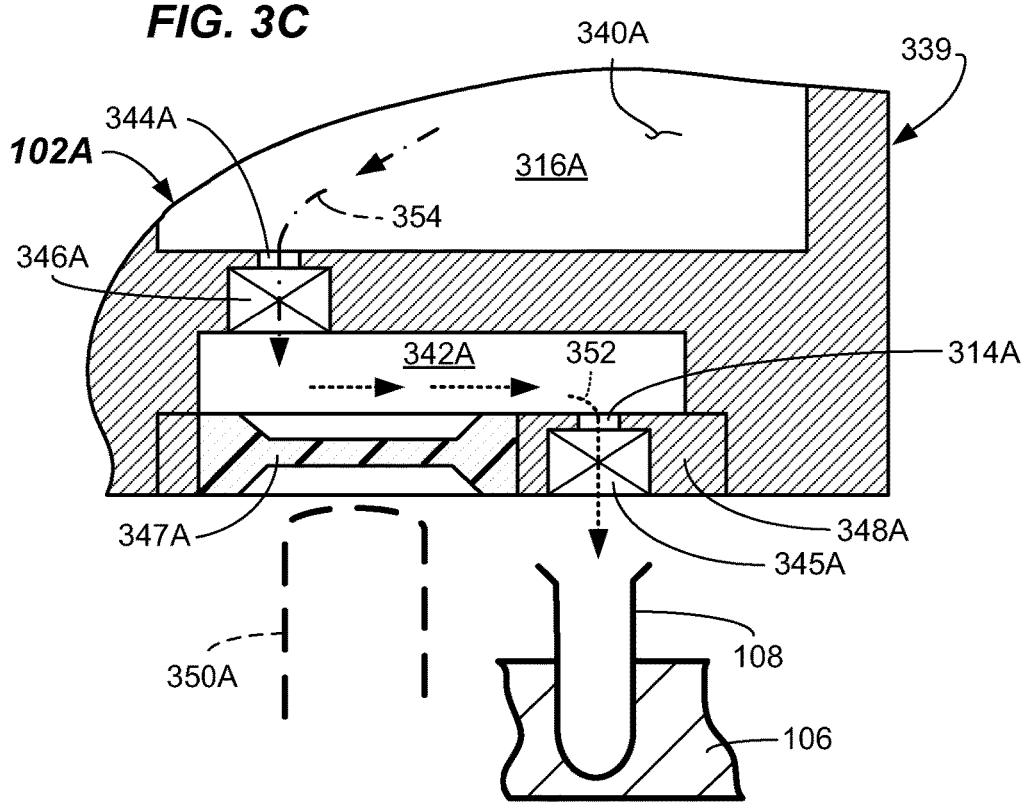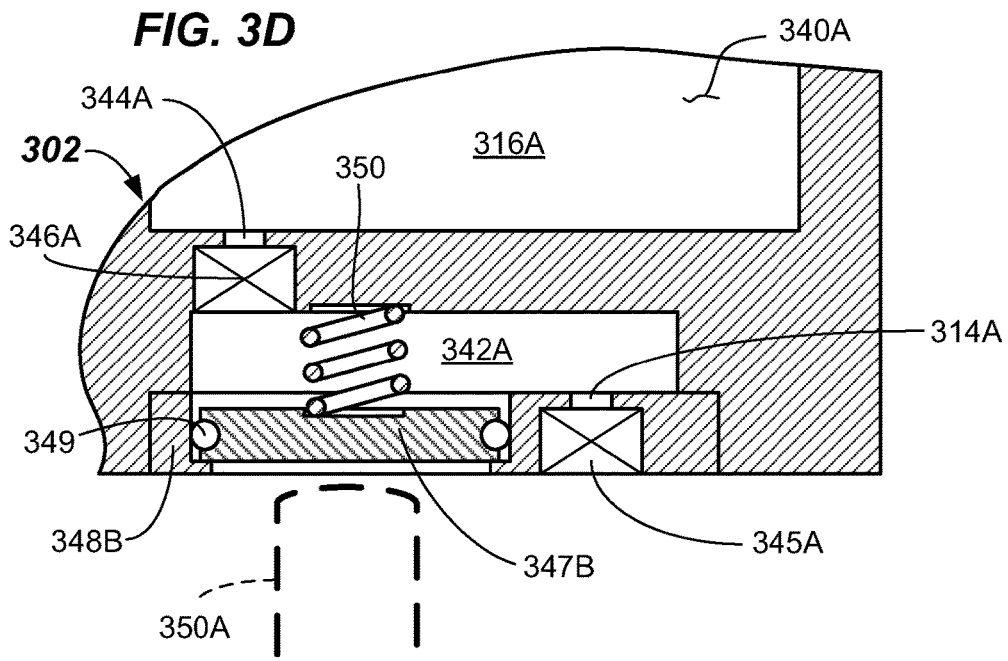

REAGENT DISPENSERS, DISPENSING APPARATUS, AND METHODS

RELATED APPLICATIONS

This application claims priority to U.S. Provisional Application Ser. No. 61/881,069 entitled "REAGENT DISPENSERS, DISPENSING APPARATUS, AND METHODS" filed on Sep. 23, 2013, and to U.S. Provisional Application Ser. No. 61/858,230 entitled "REAGENT DISPENSERS, DISPENSING APPARATUS AND METHODS" filed on Jul. 25, 2013, the disclosures of which are hereby incorporated by reference in their entirety herein.

FIELD

The present invention relates generally to reagent dispenser apparatus and methods for automated immunodiagnostic instruments.

BACKGROUND

In medical testing and processing (e.g., immunoassay testing), robotics have been used to minimize exposure to, or contact with, bodily fluid samples (otherwise referred to as "specimens") and/or to increase productivity. For example, in some existing automated testing and processing systems, reagent dispenser packs may be provided in accessible locations, such as in rotating carousels. Dispenser packs may be provided that have multiple compartments containing different reagents, for example. Likewise, sample containers (such as blood collection tubes or the like) may be provided at another location, such as in sample container racks. Conventionally, both the blood collection tubes and the reagent dispenser packs have been accessed by pipettes. Each pipette aspirates a predetermined amount of the specimen and the reagent and dispenses them into a reaction vessel (e.g., a reaction cuvette). Typically, the reagent pipette is a separate device from the sample pipette. The cuvette is then incubated for a defined period of time in an incubation ring, and may undergo a wash operation therein. The reacted sample or portion thereof is then read by a suitable testing component, such as luminometer to determine a predetermined characteristic.

Although existing immunoassay apparatus and methods may provide suitable efficiencies, more efficient and cost-effective immunoassay apparatus and methods are sought to further reduce both processing time and cost, as well as overall immunoassay apparatus cost and size. Accordingly, systems, apparatus, and methods that may improve speed and/or cost of immunoassay testing or reduce their size are desired.

SUMMARY

In a first aspect, a reagent dispenser apparatus is provided. The dispenser apparatus includes a reagent container having a dispense port operable to open and close to dispense reagent.

According to another aspect, an immunoassay apparatus is provided. The immunoassay apparatus includes a reaction vessel carrier containing one or more reaction vessel, and a dispenser support containing one or more reagent dispenser apparatus wherein at least one of the reagent dispenser apparatus includes a dispense port operable to open and close to dispense a reagent directly into the one or more of the reaction vessel located below the dispenser support.

In another apparatus aspect, a reagent dispensing apparatus is provided. The reagent dispensing apparatus includes a dispenser support, and a plurality of reagent dispenser apparatus provided in the dispenser support, wherein at least one of the reagent dispenser apparatus includes a dispense port operable to open and close to dispense a reagent.

In a method aspect, a method of dispensing a reagent is provided. The method of dispensing a reagent includes providing a reagent dispenser apparatus, and dispensing reagent from the reagent dispenser apparatus without a pipetting operation.

Still other aspects, features, and advantages of the present invention may be readily apparent from the following detailed description by illustrating a number of example embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The drawings are not necessarily drawn to scale. The invention is to cover all modifications, equivalents, and alternatives falling within the scope of the invention.

BRIEF DESCRIPTION OF THE DRAWINGS

FIG. 3C illustrates a partial cross-sectioned side view of a dispense mechanism having a dispense port operable to open and close to dispense reagent from the reagent dispenser apparatus according to embodiments.

FIG. 3D illustrates a partial cross-sectioned side view of an alternative dispense mechanism including a dispense port operable to open and close to dispense reagent from the reagent dispenser apparatus according to embodiments.

DETAILED DESCRIPTION

Figure 1A:
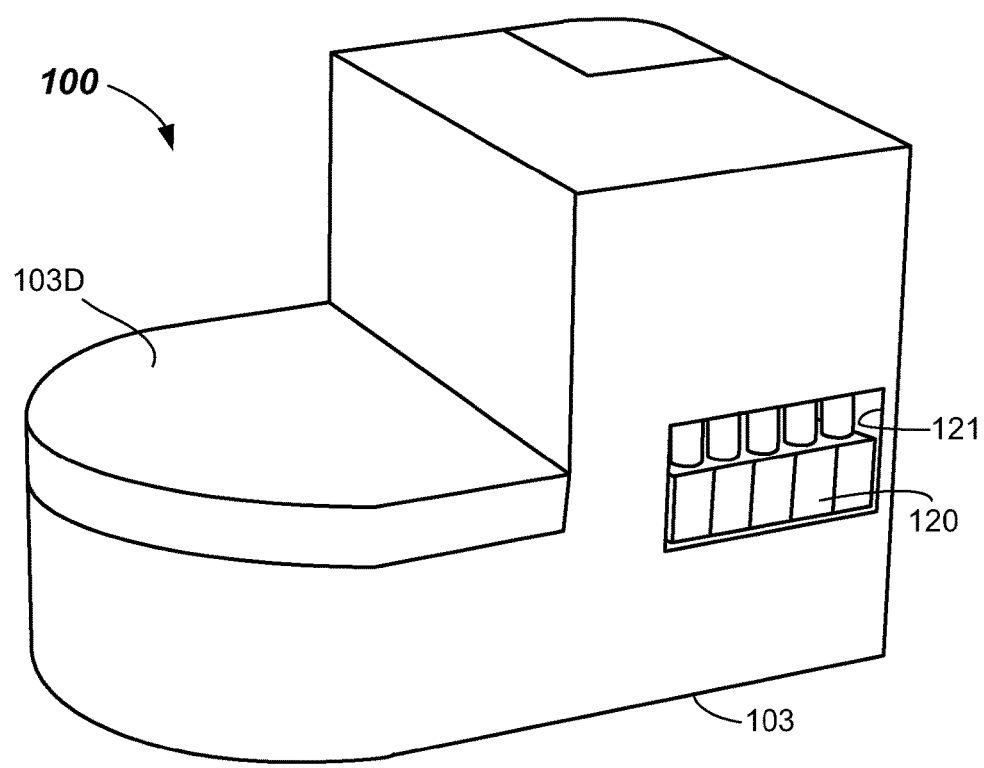
FIG. 1A illustrates an isometric view of an immunoassay apparatus according to embodiments.

In existing immunoassay apparatus, it may be desired to provide multiple reagents within a particular immunoassay instrument such that a wide variety of tests may be carried out. Prior art systems have included multi-well reagent dispenser apparatus, such as the DIMENSION® ABS FLEX® reagent cartridges available from Siemens Healthcare Diagnostics Inc. Such wells of these multi-well reagent containers may be accessed through the top by one or more aspirating probes, which may pierce a thin film that may be adhered atop of the reagent dispenser container. Multiple probes may be used in current systems to prevent reagent carryover. Moreover, separate probes may be used to dispense sample fluid (e.g., blood or blood constituent). Furthermore, existing conventional systems may have multiple probe washing stations, water backing systems per probe, and even a robot per probe in order to accomplish the desired movements of the respective probes. Such systems are therefore relatively complex requiring multiple robots to move the numerous aspirating probes between the reagent container wells, sample containers, and the reaction vessels (e.g., cuvettes), as well as multiple probe washing stations and water backing systems.

In view of the foregoing problems and complexities of conventional reagent dispenser systems, embodiments of the present invention provide reagent dispenser apparatus, reagent dispensing apparatus adapted to dispense reagent from the reagent dispenser apparatus, and dispensing methods adapted and operational to readily dispense reagent, but without requiring a dispensing probe. Accordingly, the reagent dispensing apparatus and immunoassay instrument including the reagent dispensing apparatus may be made much less complex by reducing the number of robots, number of wash stations, water backing lines and pumps, as well as the number of aspiration probes. The reagent dispensing apparatus in accordance with one or more embodiments may also reduce the overall time it takes to dispense reagent. In some embodiments, the relative size of the immunoassay instrument may be made smaller.

In a first embodiment, an immunoassay apparatus is provided. The immunoassay apparatus includes a reaction vessel carrier (e.g., a cuvette-carrying ring) containing one or more reaction vessels, and a dispenser support containing one or more reagent dispenser container wherein at least some of the reagent dispense container, and preferably all, include a dispense mechanism. The dispense mechanism may include dispense port operable to open and close to dispense a reagent. The dispense port is operable to dispense reagent directly into the one or more of the reaction vessels contained in the reaction vessel carrier located below the dispenser support. In some embodiments, the dispense mechanism may be actuatable to dispense reagent. Mechanical and pneumatic dispensing actuation is described. The actuation may comprise one to several actuation cycles in order to dispense a predefined volume "shots" of the reagent.

In another aspect, a reagent dispensing apparatus is provided having a dispenser support and one or more reagent dispenser containers provided in the dispenser support. At least one (and preferably all) of the reagent dispenser containers includes a dispense mechanism. The dispense mechanism includes a dispense port and is operable to open and close to dispense a reagent. The dispense mechanism may include a valve or other suitable structure operable to enable dispensing of reagent from, for example, a bottom of the reagent container body directly into the reaction vessel (e.g., cuvette).

In another aspect, a reagent dispenser apparatus is provided, comprising a reagent container having a dispense mechanism. The dispense mechanism includes a dispense port operable to open and close to dispense reagent.

These and other aspects and features of embodiments of the invention will be described with reference to FIGS. 1-8 herein.

Figure 1B:
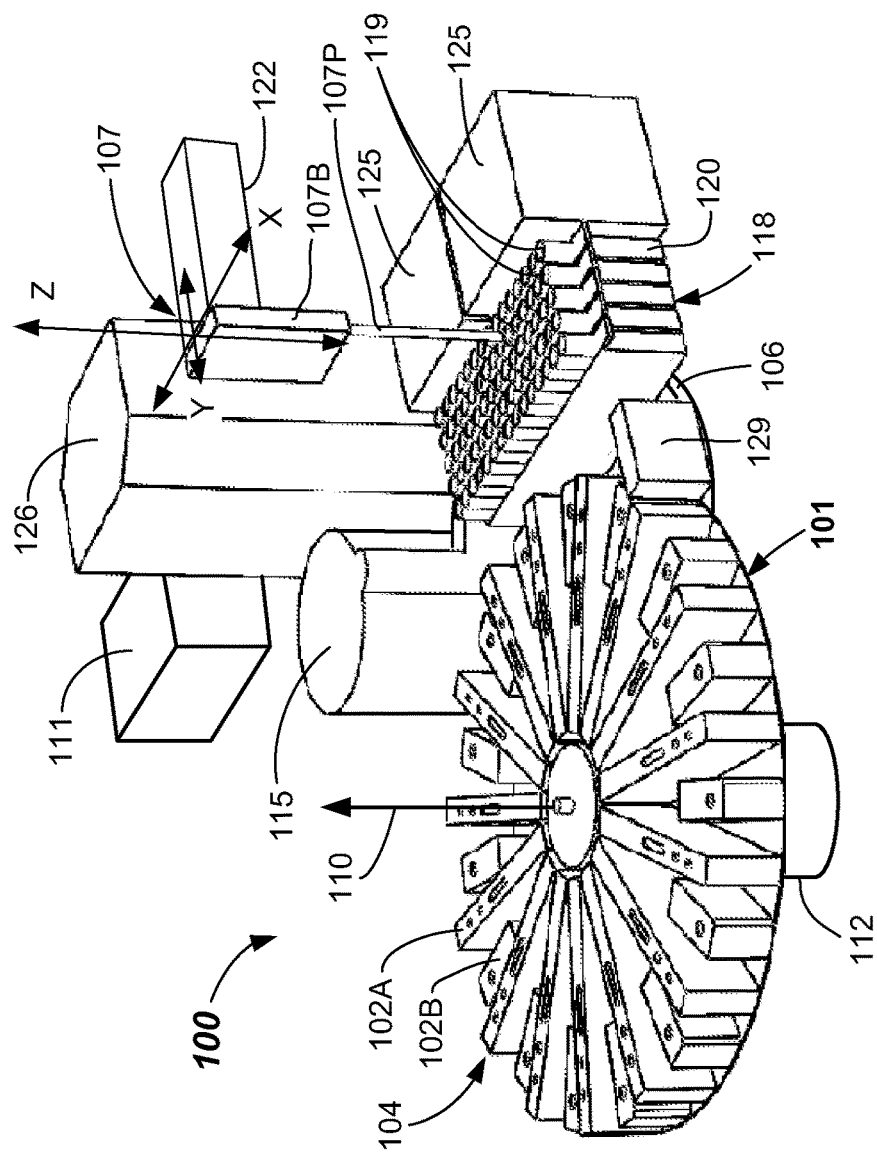
FIG. 1B illustrates an isometric view of an immunoassay apparatus with the housing removed according to embodiments.
Figure 2:
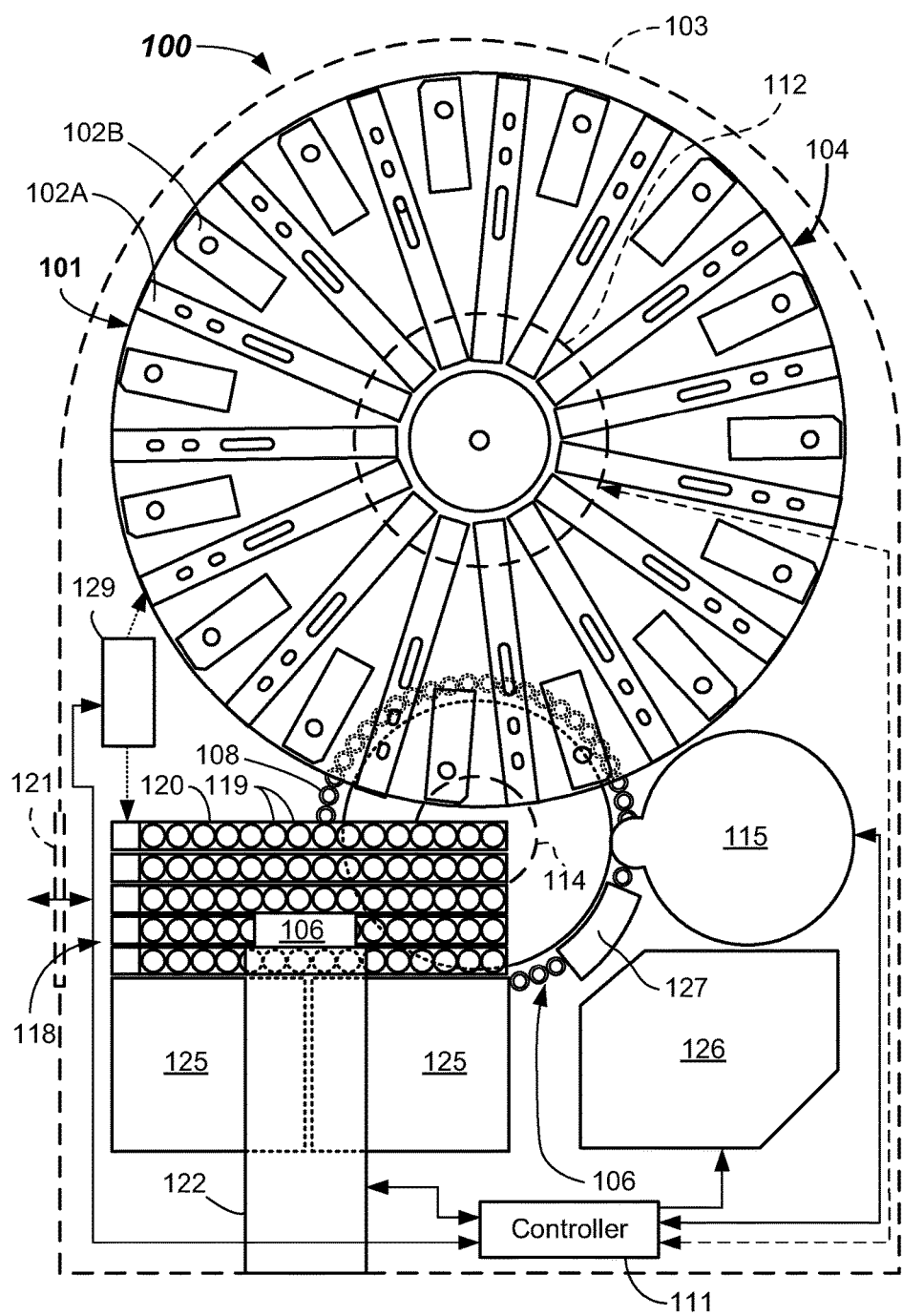
FIG. 2 illustrates a top plan schematic view of components of an immunoassay apparatus with the housing shown dotted according to embodiments.

In accordance with one or more embodiments of the invention, as best shown in FIGS. 1A, 1B, and 2, an immunoassay apparatus 100 containing an improved reagent dispensing apparatus 101 and one or more reagent dispenser apparatus 102A, 102B is described. Reagent dispensing apparatus 101 may have a single well or multiple-wells, or combinations thereof, as shown. Thus, each reagent dispenser apparatus 102A, 102B may be operational to dispense either a single reagent type or multiple reagent types. Reagent dispenser apparatus 102A, 102B may alternatively be referred to as a reagent dispenser herein. The immunoassay apparatus 100 is useful for carrying out immunoassay testing to determine the presence of a particular analyte or other material or substance of interest contained within a specimen (e.g., a sample of a biofluid).

In particular, the described embodiment includes a housing 103 (shown dotted in FIG. 2) that may fully or partially surround the various internal components. The reagent dispensing apparatus 101 may be received in the housing 103, which may be made of plastic or other suitable rigid material. The reagent dispensing apparatus 101 may be made up of at least a dispenser support 104 and a reaction vessel carrier 106, which is configured to contain one or more reaction vessels 108. The dispenser support 104, which may be in the form of a carousel, may have any suitable shape adapted to receive and position one or more reagent dispensers 102A, 102B thereon. The reaction vessel carrier 106 may have any suitable shape adapted to support one or more reaction vessels underneath the dispenser support 104.

In particular, the reagent dispensers 102A, 102B may be arranged with their long dimension oriented radially along the dispenser support 104 in some embodiments. For example, the reagent dispensers 102A, 102B may extend radially along a radius of the dispenser support 104 from a rotational axis 110 thereof. Suitable pockets or other retaining or locking features may be provided on the dispenser support 104 to position and secure the reagent dispensers 102A, 102B in a defined orientation thereon. The dispenser support 104 may be rotatable about the rotational axis 110 by a suitable dispenser support motor 112 (shown dotted) in some embodiments. Dispenser support motor 112 may be a stepper motor or the like and may receive control signals from a controller 111. Other suitable motors and/or drive systems may be used to accomplish rotation and/or positioning of the dispenser support 104. For example, in some embodiments, the dispenser support motor 112 may directly drive a shaft coupled to or integral with the dispenser support 104 and may have a rotational shaft located in line with the rotational axis 110. In other embodiments, the motor may be offset from the rotational axis 110 and drive the dispenser support 104 via a suitable drive system, such as a gear, pulley and belt, chain, worm gear, combination, or the like. Any suitable means for causing movement (e.g., rotation) of the dispenser support 104 may be used.

The dispenser support 104 includes a dispenser support body, which may be a molded body, having one or more reagent dispenser apparatus 102A, 102B mounted thereto. In particular, as shown, the dispenser support 104 may have mounted therein, a plurality of reagent dispenser apparatus 102A, 102B (a few labeled). At least some of the reagent dispenser apparatus 102A, 102B, and preferably all of them, include a dispense mechanism adapted and operational to open and close to dispense reagent. The dispense mechanism includes a dispense port, such as dispense port 314A (See FIG. 3B). The dispense port 314A may include any suitable functionality (e.g., one or more valves) that is operable to open and close the dispense port, i.e., control flow there through, to dispense a reagent 316A directly into the one or more of the reaction vessels 108. The reaction vessels 108 may be located in the reaction vessel carrier 106, wherein at least a portion of the reaction vessel carrier 106 may lie below the dispenser support 104. In the depicted embodiment, the reaction vessel carrier 106 is provided as a carrier ring configured to rotate underneath a portion of the dispenser support 104. When dispensing takes place, a particular reaction vessel 108 to receive reagent is positioned directly below particular dispense port 314A of a reagent dispenser apparatus 102A. Thus, dispensing occurs without any pipetting operation with a probe, as was the case in conventional immunoassay instruments.

As shown in FIG. 2, the footprint of the dispenser support 104 at least partially overlaps the reaction vessel carrier 106 such that dispensing of reagent 316A may be accomplished directly into a reaction vessel 108. Accordingly, the operation of dispensing a reagent 316A is substantially improved. In particular, a number of aspiration probes provided in the immunoassay apparatus 100 may be reduced, a number of probe wash stations may be reduced, water backing systems may be reduced, and dispensing speed may possibly be increased.

In one or more embodiments, the reaction vessel carrier 106 may comprise a carrier ring having a plurality of receptacles (e.g., pockets or the like) configured to receive reaction vessels 108 and rotate them underneath a portion of the dispenser support 104. Reaction vessel carrier 106 comprising a carrier ring may hold the reaction vessels 108 (e.g., clear cuvettes) and provide them in a circle-shaped orientation arranged at a common radius. More than one radius may be provided in some embodiments, wherein a first plurality of reaction vessels may be provided at a first radius, and a second plurality of reaction vessels may be provided at a different radius. Reaction vessel carrier 106 may include any suitable construction enabling the carrying of reaction vessels 108, and may include a plurality of suitable receptacles adapted to receive reaction vessels 108 therein. Like dispenser support 104, reaction vessel carrier 106 may be rotated incrementally by a suitable rotational member, such as carrier motor 114 (shown dotted in FIG. 2). Carrier motor 114 may be a stepper motor or other motor as described for the dispenser support 104. Rotation of the reaction vessel carrier 106 may be controlled via control signals from the controller 111.

Again referring to FIGS. 1B, and 2, the immunoassay apparatus 100 includes a specimen staging area 118. Specimens contained in specimen containers 119 (e.g., sample tubes or blood collection vessels) may be provided to the specimen staging area 118 in one or more sample racks 120. In the depicted example, the sample rack 120 is a 15×5 position rack enabling the processing of 75 specimens. Other sizes of sample racks 120 may be used. One or more than one sample rack may be provided at the specimen staging area 118. The one or more sample racks 120 may be inserted into and/or removed from the immunoassay apparatus 100 through an opening 121 formed in the housing 103. Opening 121 may include an opening, removable or openable door in some embodiments. Locating features (not shown) within the immunoassay apparatus 100 may function to precisely position the one or more sample racks 120 within the interior of the immunoassay apparatus 100, and may secure it to a portion of the housing 103 or an internal frame of the immunoassay apparatus 100, for example.

A sample probe 107 may also be provided within the immunoassay apparatus 100. The sample probe 107 may include a proboscis portion 107P and a body 107B. The body 107B may be connected to a pump or other source of vacuum pressure (not shown) such that specimen aspiration may take place. Suitable configurations of aspiration systems which may be used with embodiments of the present invention are described in U.S. Pat. Nos. 7,867,769; 7,634,378; 7,477,997; 7,186,378; 7,150,190; and 6,370,942, for example. Other suitable aspiration systems may be used.

The body 107B may be coupled to, and moved by, a suitable robot 122, which may be coupled to the housing 103 either directly, or through an internal frame. The robot 122 may be any suitable robot adapted to move the sample probe 107 from the specimen containers 119 at the specimen staging area 118 to the reaction vessel 108 resident in the reaction vessel carrier 106. The robot 122 may be a multi-arm robot, a gantry robot, or the like. Other types of robots may be used. The robot 122 may include suitable elements to accomplish three-dimensional motion of the proboscis portion 107P of the sample probe 107. For example, the robot 122 may be capable of motion in the X, Y and Z directions as shown. The means for moving the sample probe 107 may include any suitable conventional motion-producing mechanism, such as one or more stepper motors, servo motors, pneumatic or hydraulic motors, electric motors, or the like. Furthermore, drive systems including chains, guides, pulleys and belt arrangements, gear or worm drives or other conventional drive components may be utilized to cause the motion of the sample probe 107.

Adjacent to the specimen staging area 118, may be one or more probe tip supply 125 that includes probe tips that may be picked up by the proboscis portion 107P. Immunoassay apparatus 100 may include a reaction vessel supply 126, which may be a cuvette loader, for example. Reaction vessel supply 126 may be a conventional cuvette loader and is operational to load reaction vessels 108 into the reaction vessel carrier 106.

The immunoassay apparatus 100 also includes a test component 115, that may determine an analyte, substance, or characteristic, or the like of the reaction fluid contained in the reaction vessel 108, such as after undergoing a reaction. For example, in some embodiments, test component 115 may be an apparatus (e.g., a luminometer) that operates to measure luminescence of the reaction sample through a reaction vessel 108 (e.g., a clear cuvette). In some embodiments, the testing is carried out while the reaction vessel 108 is resident in reaction vessel carrier 106. In other embodiments, an elevator may be used to lift or remove the reaction vessel 108 from the reaction vessel carrier 106 during the test. In some embodiments, the test component 115 may send a light signal and determine therefrom (e.g., via a sensor) another characteristic of the reaction fluid (containing specimen, one or more reagents, and possibly a dilutant). For example, the test component 115 may determine luminescence, absorbance, or the like of the reaction fluid contained in the reaction vessel 108. Other types of testing may be carried out on the reaction liquid in the reaction vessel 108. For example, photometric, turbidimetric, chemiluminescence, nephelometric, or other testing may be carried out. More than one test component 115 may be provided. The test component 115 may be tested after undergoing a suitable incubation period and wash process at wash station 127 while resident in reaction vessel carrier 106. The reaction process carried out in the reaction vessel 108 and wash process carried out in wash station 127 are entirely conventional.

The immunoassay apparatus 100 may also include an identification reader 129, such as a barcode reader, or any suitable identification code, indicia, device, or the like. The identification reader 129 may be provided at any suitable position to enable identification of, for example, the sample rack 120 that has been inserted into the immunoassay apparatus 100. Identification of, and location of the individual specimen containers 119 in the sample rack 120 may be known based upon stored data that is contained in, or assessable by, the controller 111. The identification reader 129 may also read codes (e.g., barcodes, indicia or other identification devices) located on one or more (preferably all) of the reagent dispenser apparatus 102A, 102B mounted on the dispenser support 104. This allows the type of reagent contained therein, and possibly other information about the reagent dispenser apparatus 102A, 102B, such as the location, number of dispensed shots, and/or lot number, manufacture date, calibration data, or the like to be readily accessed and/or verified. As the dispenser support 104 is first mounted in the immunoassay apparatus 100, the dispenser support 104 may be rotated so that each reagent dispenser apparatus 102A, 102B passed by the identification reader 129 so that the identity, location, and/or content of the reagent dispenser apparatus 102A, 102B may be determined and stored in memory of the controller 111. As the reagent in the reagent dispenser apparatus 102A, 102B becomes all used up, the dispenser support 104 may be removed, refilled, and then replaced in the immunoassay apparatus 100. A door 103D above the dispenser support 104, which may be removable or hinged, may be provided.

Figure 3A:
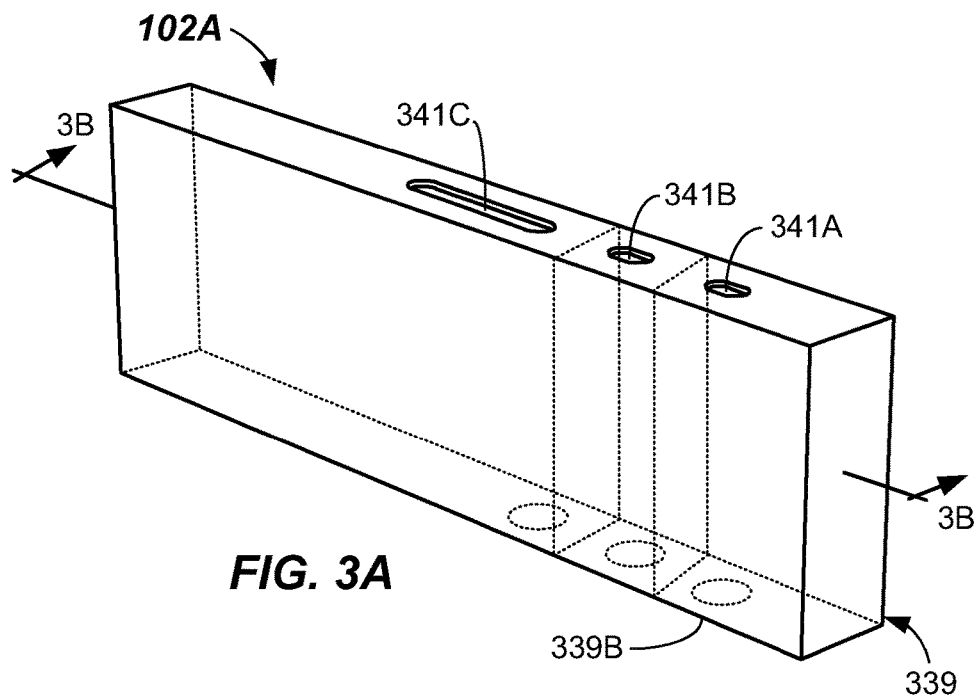
FIGS. 3A and 3B illustrate isometric and cross-sectioned side views, respectively, of a reagent dispenser apparatus according to embodiments.
Figure 3B:
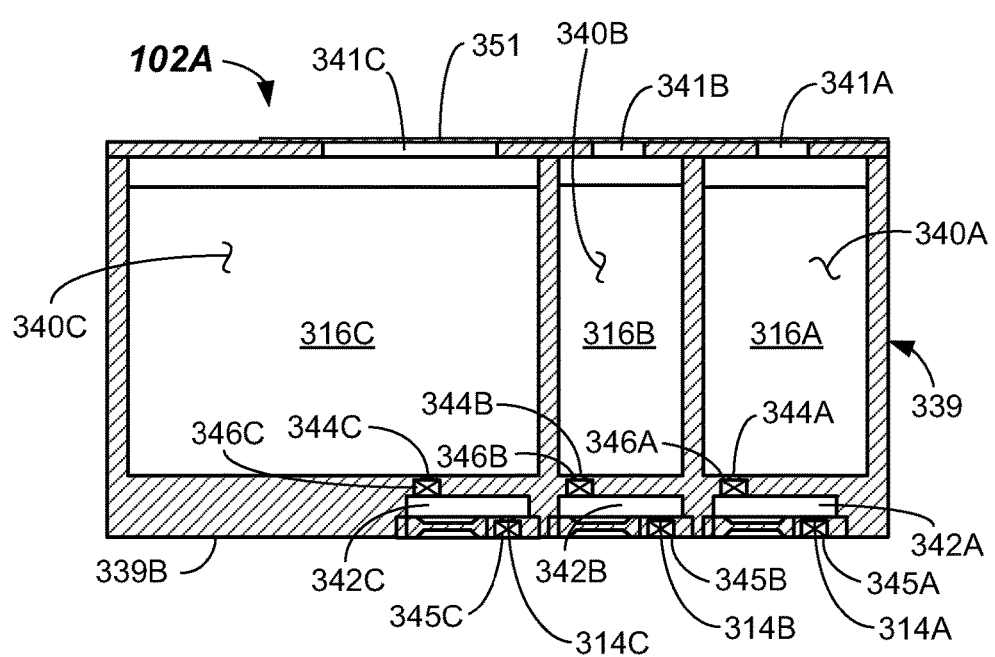

An embodiment of a reagent dispenser apparatus 102A in accordance with another aspect of the invention will now be described with reference to FIGS. 3A-3C. Reagent dispenser apparatus 102A includes a reagent container formed by a container body 339 with one or more reagent storage chambers (e.g., 340A, 340B, and 340C) formed by external and internal walls therein. Each reagent storage chamber (e.g., 340A, 340B, and 340C) may contain a different type of reagent. A reagent is a substance used in a chemical reaction to detect, measure, examine, or produce another substance(s). The reagent may be a chemiluminescence reagent (e.g., chemiluminescence phases such as solid, lite, and buffer solutions), a mitigation agent (such as NaCOI), or the like. A diluting agent (e.g., water) may also be dispensed as part of a chemical or biological reaction in a reaction vessel 108 along with the reagent. Reagents, as used herein, are dispensed materials that are used in an immunoassay reaction. The number of agent storage chambers may be one (e.g., FIG. 4) or more than one (such as three shown in FIGS. 3A-3B). Other numbers of reagent storage chambers may be used.

The reagent dispenser apparatus 102A further includes a dispense mechanism. The dispense mechanism may include a dispense port (e.g., 314A, 314B, 314C) associated with some or all of the reagent storage chambers (e.g., 340A, 340B, and 340C). Dispense ports (e.g., 314A, 314B, 314C) are operable to open and close to dispense reagent (e.g., reagent 316A, 316B, 316C) from the respective reagent storage chambers (e.g., 340A, 340B, and 340C). "Open" as used herein refers to a condition where flow through a particular dispense port (e.g., 314A, 314B, 314C) is allowed, whereas "close" as used herein refers to a condition where flow through the dispense port (e.g., 314A, 314B, 314C) is not allowed. For a single reagent dispense operation, the dispense port 314A may be opened once and closed once, for example. Once opened, a defined amount (e.g., volume) of reagent 316A may be dispensed. This is otherwise referred to herein as a "shot" of reagent. Defined amounts (e.g., shots) of reagents 316B, 316C may likewise be dispensed by opening and closing of dispense ports 314B, 314C. Dispense operations may be directly into a reaction vessel 108.

In the depicted embodiment, the dispense mechanism includes one or more reagent dispense chambers (e.g., 342A, 342B, 342C). Reagent dispense chambers (e.g., 342A, 342B, 342C) are shown coupled (e.g., fluidly connected) to the respective reagent storage chambers (e.g., 340A, 340B, and 340C) by one or more inlet ports (e.g., inlet ports 344A, 344B, 344C). Inlet ports 344A, 344B, 344C are flow passages that allow reagent 316A, 316B, 316C to flow from the respective reagent storage chambers 340A, 340B, and 340C to the reagent dispense chambers 342A, 342B, 342C. Reagent dispense chambers 342A, 342B, 342C may have a contained volume of, for example, between about 10 μl and about 400 μl. Reagent storage chambers 340A, 340B, 340C may have a contained volume of, for example, between about 5 ml and about 75 ml. Other volumes may be used. In one or more embodiments, the contained volume of the respective reagent storage chambers (e.g., 340A, 340B, and 340C) is much larger than the contained volume of the reagent dispense chambers (e.g., 342A, 342B, 342C).

Dispense ports 314A, 314B, 314C may include a dispense valve 345A, 345B, 345C either therein or operable therewith. Dispense valve 345A, 345B, 345C may be any suitable valve that may control flow of reagent 316A, 316B, 316C from the reagent dispense chambers 342A, 342B, 342C. For example, the dispense valve 345A, 345B, 345C may be a one-way valve, i.e., allowing flow in one direction only (e.g., out of the respective reagent dispense chambers 342A, 342B, 342C, for example). The dispense valve 345A, 345B, 345C may be a check valve, for example. The dispense valve 345A, 345B, 345C may be a spring-loaded ball valve, a poppet valve, a reed valve, a membrane valve, or the like. Other suitable types of one-way valves may be used. Dispense valve 345A, 345B, 345C may be passive, that is, containing only passive components that open flow in response to a predesigned pressure increase. For example, dispense valve 345A, 345B, 345C may open if the pressure in the reagent dispense chamber exceeds about 10 psi, for example. Other suitable opening pressures may be used. Dispense valve 345A, 345B, 345C may be located proximate to a bottom surface 339B of the container body 339. In particular, the dispense ports 314A, 314B, 314C may exit directly from a bottom (e.g., bottom surface 339B) of the container body 339 in some embodiments.

In the depicted embodiment, an inlet valve 346A, 346B, 346C may be included in, or operative with, the inlet ports 344A, 344B, 344C. Inlet valve 346A, 346B, 346C may be operable to control and limit flow of reagent through the inlet ports 344A, 344B, 344C, which connect the respective reagent storage chambers 340A, 340B, 340C and the respective reagent dispense chambers 342A, 342B, 342C. Inlet valve 346A, 346B, 346C may be one-way valve, and may be the same or different construction than the dispense valve 345A, 345B, 345C. In the depicted embodiment, the container body 339 has the plurality of dispense ports 314A, 314B, 314C spaced along a length thereof. These dispense ports 314A, 314B, 314C may positioned so as to be aligned with desired ones of the reaction vessels 108 that are mounted in the reaction vessel carrier 106 by appropriate motions (e.g., rotations) of the dispenser support 104 and the reaction vessel carrier 106.

For example, in the depicted embodiment, rotation of the dispenser support 104 and the reaction vessel carrier 106 may be coordinated to vertically align dispense port 314C with a desired reaction cuvette 108 that is to receive the reagent 316C. Likewise, dispense port 314B may be aligned with a desired reaction cuvette 108 that is to receive the reagent 316B, and dispense port 314A may be aligned with a desired reaction cuvette 108 that is to receive the reagent 316A. Through appropriate coordinated rotations of the dispenser support 104 and reaction vessel carrier 106, any one reaction cuvette 108 may then receive one, more than one, or even more than two reagents. Reagent may be received from a single reagent dispenser apparatus adapted to contain an auxiliary reagent (e.g., reagent dispenser apparatus 102B) or from a multiple reagent dispenser apparatus (e.g., reagent dispenser apparatus 102A).

In operation, the depicted embodiment of dispenser apparatus 102A, as shown in FIG. 3C, includes the reagent dispense chamber 342A having an inlet port 344A and dispense port 314A. The dispense mechanism includes an inlet valve 346A (e.g., a one-way valve) controlling flow through the inlet port 344A, and a dispense valve 345A (e.g., a one-way valve) controlling flow through the dispense port 314A. The reagent dispense chamber 342A may include a moveable wall 347A adapted to change a volume of the reagent dispense chamber 342A. The moveable wall 347A may comprise a flexible diaphragm, bellows, or other flexible member.

Moveable wall 347A may be made of any suitable flexible material, such as a polymer (e.g., rubber, silicone, or the like). Moveable wall 347 may be molded or bonded to a closure member 348A, which may have the dispense port 314A and dispense valve 345A formed or received thereon. Actuation of the moveable wall 347A, such as by an actuation member 350A (shown dotted), causes movement of the moveable wall 347A. Upward movement of the actuation member 350A displaces reagent 316A from the reagent dispense chamber 342A, as shown by first dotted arrows 352, into a reaction vessel 108 positioned in the reaction vessel carrier 106 directly vertically below the dispense port 314A. Actuation member 350A may be a rod or other suitable displaceable member coupled to an actuator, such as a solenoid, piezoactuator, or the like. Actuation of the actuation member 350A through a predefined translational distance (e.g., stroke) in the upward direction flexes and displaces the moveable wall 347A and thereby displaces a known amount of reagent 316A (i.e., a "shot" of reagent 316A) from the reagent dispense chamber 342A into the reaction vessel 108, as shown by first dotted arrows 352.

Retraction motion of the actuation member 350A downward through a defined return distance draws in another "shot" of the reagent 316A into the reagent dispense chamber 342A from the reagent storage chamber 340A through inlet port 344A and inlet valve 346A as shown by second dotted arrows 354. Actuation of the actuation member 350A may be carried out once to dispense a single "shot" or multiple times to dispense multiple "shots" of the reagent 316A into a particular reaction vessel 108 that has been vertically aligned with the dispense port 314A through appropriate coordinated rotations of the dispenser support 104 and reaction vessel carrier 106.

FIG. 3D illustrates another embodiment of a reagent dispenser apparatus 302 that includes reagent dispense chamber 342A having an inlet port 344A and dispense port 314A. The dispense mechanism includes an inlet valve 346A (e.g., a one-way valve) controlling flow through the inlet port 344A, and a dispense valve 345A (e.g., a one-way valve) controlling flow through the dispense port 314A. The reagent dispense chamber 342A includes a moveable wall 347B adapted to change a volume of the reagent dispense chamber 342A. The moveable wall 347B in this embodiment may comprise a puck that is sealed to a closure member 348B, by a suitable sealing member 349 (e.g., O-ring, lip seal or other suitable sealing member). Upward motion of the actuation member 350A causes movement of the moveable wall 347B and displaces reagent 316A from reagent dispense chamber 342A. Spring 350 returns the moveable wall upon retraction of the actuation member 350A and draws in a new shot of reagent 316A from the reagent storage chamber 340A.

Figure 4:
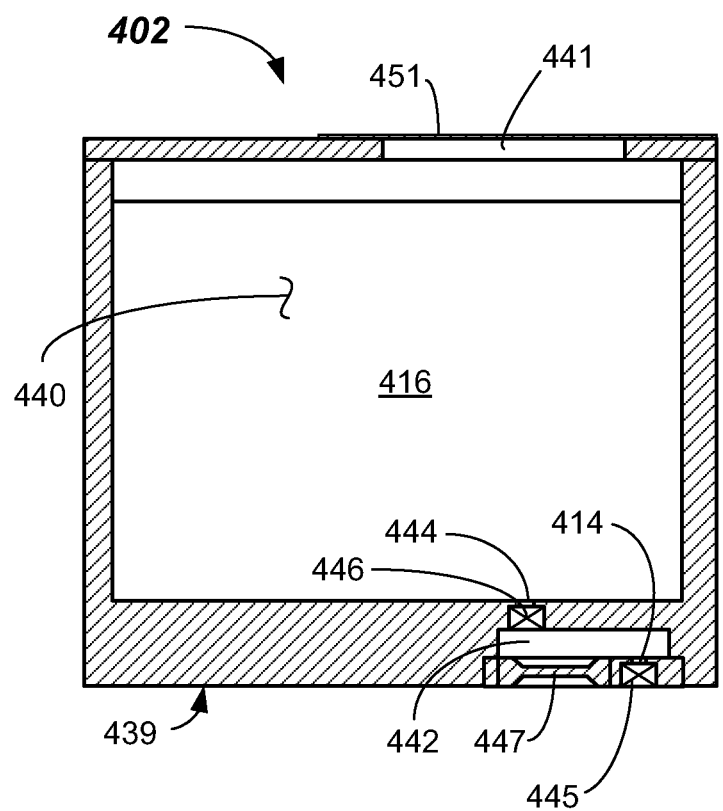
FIG. 4 illustrates a cross-sectioned side view of a single reagent dispenser apparatus adapted to dispense only a single reagent type according to embodiments.

FIG. 4 illustrates an embodiment of a single-reagent dispenser apparatus 402 that includes reagent dispense chamber 442 having an inlet port 444 and dispense port 414. The dispense mechanism includes an inlet valve 446 (e.g., a one-way valve) allowing flow into the inlet port 444 when sufficient pressure differential across the valve is present, but not allowing backflow, and a dispense valve 445 (e.g., a one-way valve) controlling flow out of the dispense port 414 once sufficient pressure is reached. The reagent dispense chamber 442 includes a moveable wall 447 adapted to change a volume of the reagent dispense chamber 442. The moveable wall 447 in this embodiment may comprise any of the previously-disclosed structures. Upward motion of an actuation member (not shown) contacts the moveable wall 447 and displaces reagent 416 from reagent dispense chamber 442. Upon retraction of the actuation member, a new shot of reagent 416 from the reagent storage chamber 440 is drawn into the reagent dispense chamber 442 so that it is now ready for another shot dispense.

In the depicted embodiment, a top of the container body 439 may include a top opening 441 adapted to receive a probe therein, should the reagent dispenser apparatus 402 be used in a conventional, probe-aspirated system. Thus, as configured, the reagent dispenser apparatus 402 is capable of either top probe aspiration or bottom probe-less aspiration. However, it should be understood that in a reagent dispensing apparatus as described herein, the top opening 441 may not be present. In the case where the top opening 441 is present to allow use in conventional, probe-aspirated systems, the top opening 441 may be covered with a sealing sheet 451, such as with an adhesive-backed foil. Likewise, such openings 341A-341C may also be present in the multi-chamber configurations, as shown in FIGS. 3A and 3B to allow use in either conventional, probe-aspirated systems, or the inventive bottom-aspirated systems as described herein. Likewise, dispenser apparatus 102A may include a sealing sheet 351 covering and sealing the openings 341A-341C. Sealing sheet is not shown in FIG. 3A, for clarity.

Figure 5A:
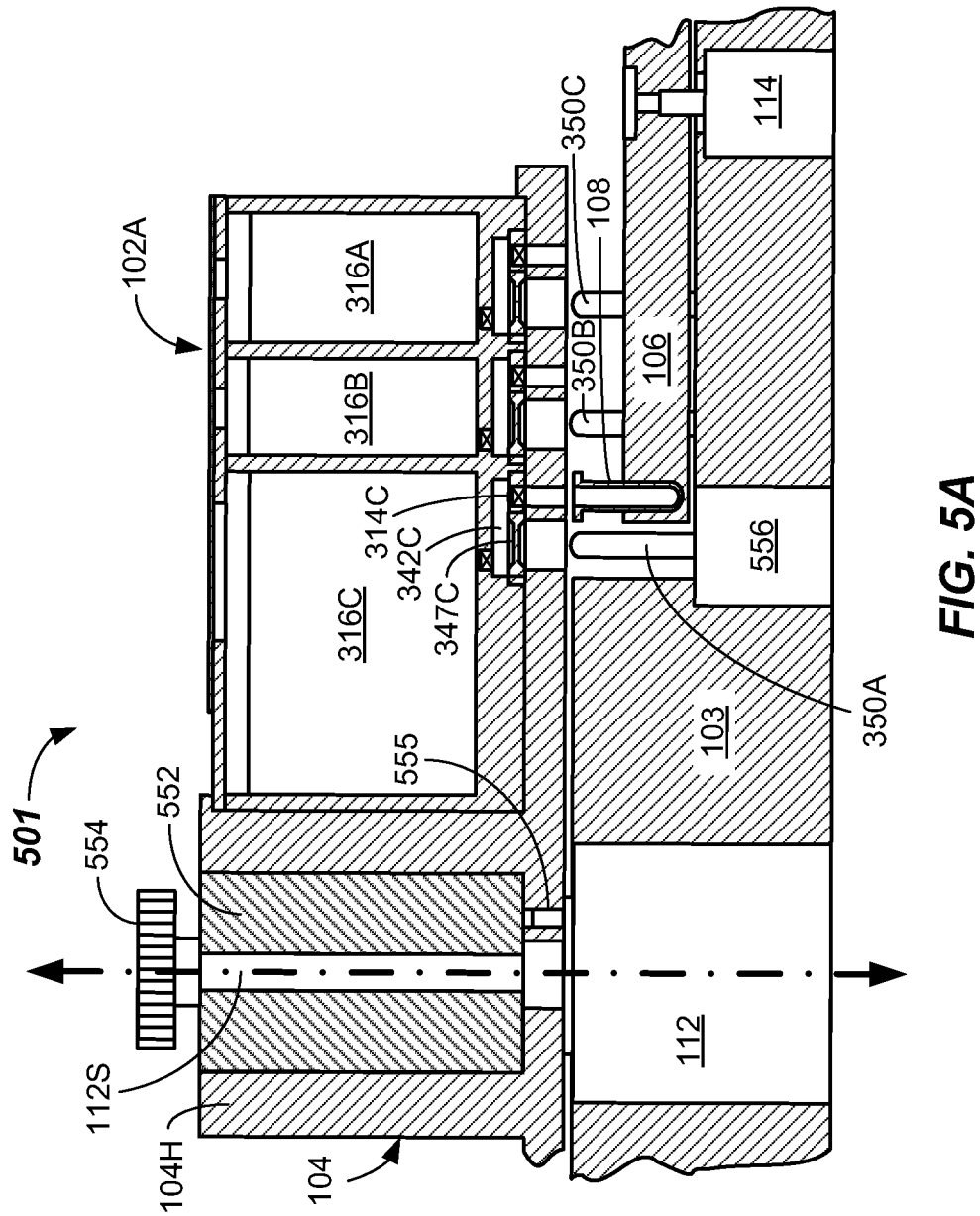
FIG. 5A illustrates a partial cross-sectioned side view of a reagent dispensing apparatus including a reagent dispenser apparatus according to embodiments.
Figure 5B:
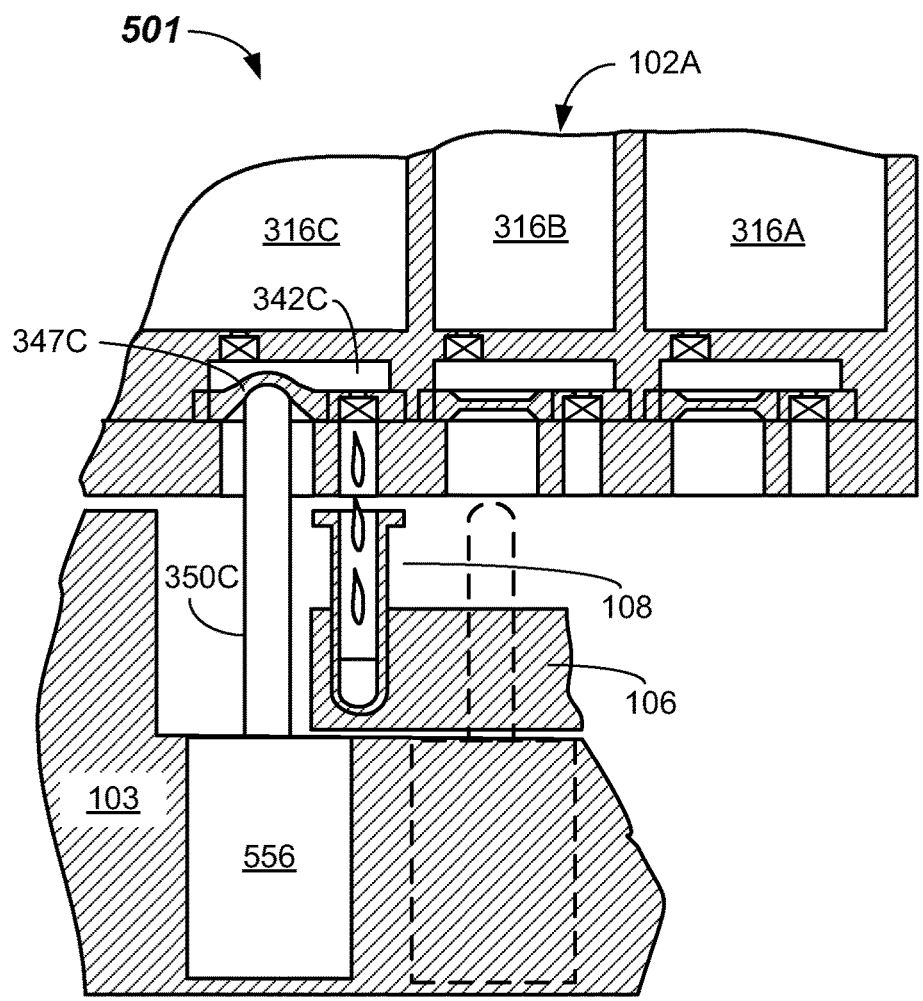
FIG. 5B illustrates a partial cross-sectioned side view of a reagent dispensing apparatus in the act of dispensing a reagent into a reaction vessel from a reagent dispenser apparatus according to embodiments.

FIGS. 5A-5B illustrates a partial cross-sectioned side view of a reagent dispensing apparatus 501 including a reagent dispenser apparatus 102A according to embodiments. Reagent dispensing apparatus 501 may be included in an immunoassay apparatus 100 as described herein. As shown, the reagent dispensing apparatus 501 includes a dispenser support 104 (a portion shown), and one or more reagent dispenser apparatus 102A provided in the dispenser support 104. The reagent dispensing apparatus 102A may be provided in the dispenser support 104 by being registered on one or more features, such as lips, recesses, posts, or the like. Locking features may be provided, such as snap-fit locking tabs or other suitable locking structure that secures the reagent dispenser apparatus 102A to the dispenser support 104. The reagent dispenser apparatus 102A includes a dispense port 314C, as shown, operable to open and close to dispense a reagent 316. The dispense port 314C remains closed (no flow) when the pressure in the reagent dispense chamber 342C is below a predesigned threshold pressure, and the dispense port 314C is opened (flowing) when the pressure in the reagent dispense chamber 342C is above predesigned threshold pressure. As shown, the dispenser support 104 with the attached one or more reagent dispenser apparatus 102A, is removable from the housing 103. The dispenser support 104 may include a hub 104H that receives a locking member 552 therein. Locking member 552 may be contacted by a fastening member 554 (e.g., a threaded knob) to secure the dispenser support 104 to a shaft 112S of the dispenser support motor 112. A rotation registering feature 555 (e.g., a pin or other feature) may be used to allow the dispenser support 104 to be mounted on the shaft 112S in only one rotational orientation. Rotation registering feature 555 may be a pin mounted in a shoulder of the shaft 112S. Other suitable rotation registry features may be used.

To dispense reagent 316C, the reaction vessel carrier 106 containing a reaction vessel 108 is rotated by carrier motor 114 and the dispenser support 104 is rotated by dispenser support motor 112 to appropriate rotational orientations to vertically align the reaction vessel 108 below the dispense port 314C. The actuation member 350A may then be actuated by actuator 556 to move the moveable wall 347C as shown in FIG. 5B, which dispenses a predetermined volume (e.g., a shot) of the reagent 316C directly into the reaction vessel 108. A respective actuator and actuator member (e.g., 350A, 350B, and 350C) may be provided at different position to accomplish the dispensing for each reagent 316A, 316B, 316C in the reagent dispenser apparatus 102A.

Figure 6:
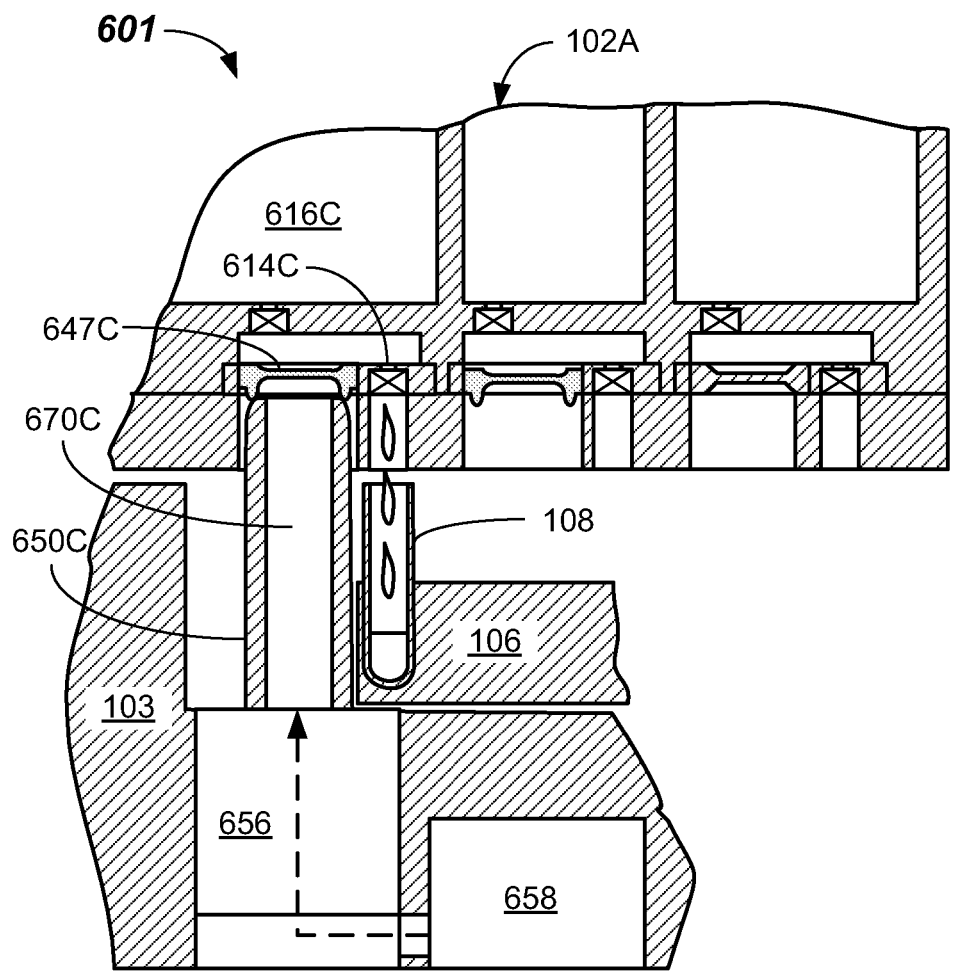
FIG. 6 illustrates an alternative embodiment of a reagent dispensing apparatus including pneumatic actuation of the reagent dispenser apparatus according to embodiments.

FIG. 6 illustrates a partial cross-sectioned side view of another alternative embodiment of a reagent dispensing apparatus 601 including a reagent dispenser apparatus 102A according to embodiments. The depicted reagent dispensing apparatus 601 includes pneumatic actuation of the moveable wall 647C. The actuator 656 moves the actuation member 650C into sealed contact with the moveable wall 647C, which may be an elastomer bladder or the like. Once extended into sealed contact, a pneumatic source 658, such as an air pump, may be operated to provide a predetermined gas pressure in a passage 670C in the actuation member 650C, which flexes the moveable wall 747C and causes a shot of the reagent 316C to be dispensed into the reaction vessel 108 located below the dispense port 614C. Pneumatic and mechanical actuation apparatus have been described herein. However, any suitable actuation technique that causes reagent to be dispensed from the reagent storage 616C into the reaction vessel 108 without a pipetting operation may be used.

Figure 7:
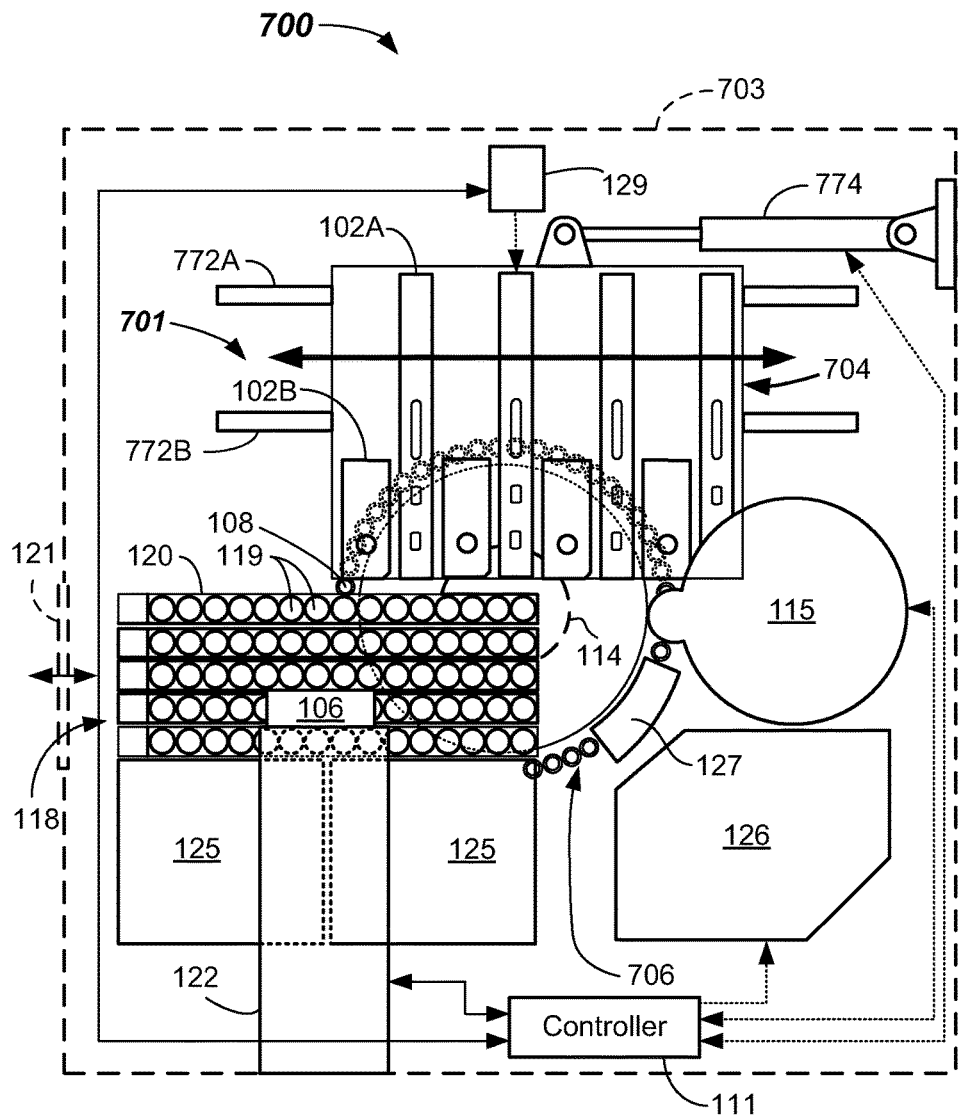
FIG. 7 illustrates a top plan schematic view of components of an alternate immunoassay apparatus according to embodiments.

FIG. 7 illustrates another embodiment of immunoassay apparatus 700. In this embodiment, a dispenser support 704 of the reagent dispensing apparatus 701 having one or more dispenser apparatus 102A, 102B mounted thereon is non-rotary acting, rather than rotary acting as in the previous embodiments. The dispenser support 704 may move along a non-rotary path (e.g., linearly along a linear path) on one or more path restraints, such as guide rails 772A, 772B shown. Again, the dispenser support 704 overlaps the reaction vessel carrier 706 such that an agent (e.g., a reagent) may be dispensed directly into a reaction vessel 108 mounted in the reaction vessel carrier 706 below the dispenser support 704. Non-rotary motion may be produced by an actuator 774 coupled between the housing 703 (or to a frame member with the housing 703) and the dispenser support 704. Any suitable actuator 774 may be used, such as a linear variable displacement transducer (LVDT) or the like. The other components of the immunoassay apparatus 700 may be as discussed above. Thus, in this embodiment, one or more agents (e.g., reagent) may be dispensed directly into a reaction vessel 108 from a dispense port (e.g., outlet) without a pipetting operation. As shown, linear actuation of the dispenser support 704 coupled with coordinated rotation of the reaction vessel carrier 706 can align any desired dispense port of any desired reagent dispenser apparatus 102A, 102B with any desired reaction vessel 108.

Figure 8:
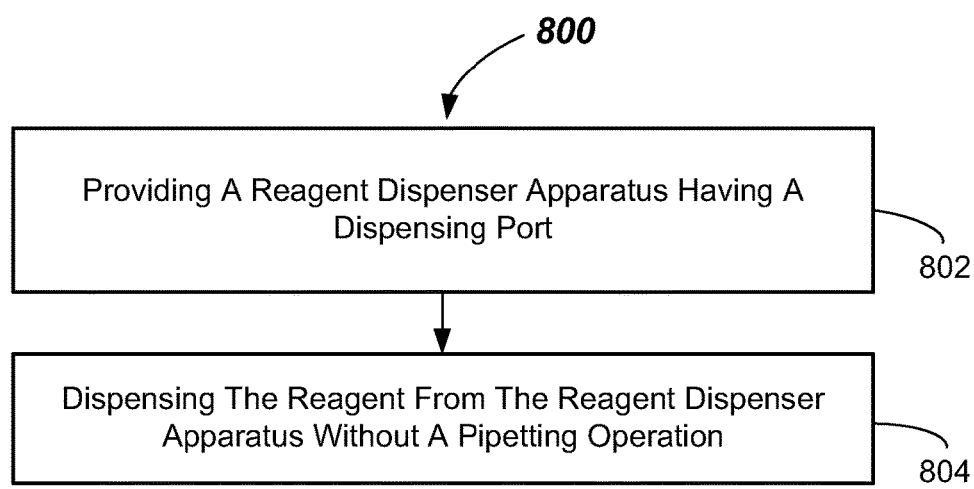
FIG. 8 illustrates a flowchart of a dispensing method according to embodiments.

An embodiment of a method of dispensing a reagent (e.g., 316A, 316B, 316C, 414, 614C) into a reaction vessel (e.g., reaction vessel 108) will now be described with reference to FIG. 8. The method 800 includes, in 802, providing a reagent dispenser apparatus (e.g., reagent dispenser apparatus 102A, 102B, 302, 402) having a dispense port (e.g., dispense port 314A, 314B, 314C, 414, 614C).

The method 800 includes, in 804, dispensing the reagent from the reagent dispenser apparatus without a pipetting operation. In particular, the reagent is dispensed directly from the reagent dispenser apparatus into the reaction vessel through a dispense port. Reagent may flow from a reagent storage chamber to a reagent dispense chamber and then into the reaction vessel from the dispense port in some embodiments.

While the invention is susceptible to various modifications and alternative forms, specific system and apparatus embodiments and methods thereof have been shown by way of example in the drawings and are described in detail herein. It should be understood, however, that it is not intended to limit the invention to the particular systems, apparatus, or methods disclosed but, to the contrary, the intention is to cover all modifications, equivalents, and alternatives falling within the scope of the invention.

What is claimed is:

1. An immunoassay apparatus, comprising:
   a reaction vessel carrier containing one or more reaction vessels; and
   a dispenser support containing one or more reagent dispenser apparatus wherein at least one of the reagent dispenser apparatus includes:
      a reagent dispense chamber having a vertically moveable wall adapted to change a volume of the reagent dispense chamber by upward movement of the vertically moveable wall;
      a dispense port connected to the reagent dispense chamber and operable to open and close to dispense a reagent downward directly into the one or more of the reaction vessels located vertically below the dispenser support; and
      an inlet port and a first one-way valve, the inlet port vertically offset from the dispense port, and the first one-way valve configured to control reagent flow through the inlet port and into the reagent dispense chamber; and
   an actuator configured to move an actuation member to move the moveable wall upward to change the volume of the reagent dispense chamber, the dispenser support being laterally moveable relative to the actuator; and
   a dispenser support motor configured to move the dispenser support to where the actuator is located beneath the vertically moveable wall of the at least one reagent dispenser apparatus.

2. The immunoassay apparatus of claim 1, wherein the reaction vessel carrier comprises a carrier ring configured to rotate underneath a portion of the dispenser support.

3. The immunoassay apparatus of claim 1, wherein the actuation member is adapted to engage the moveable wall from beneath the dispenser support to cause dispense of the reagent directly into the one or more of the reaction vessels.

4. The immunoassay apparatus of claim 1, wherein the reaction vessel carrier is laterally moveable relative to the actuator.

5. The immunoassay apparatus of claim 1, further comprising a dispense valve configured to control the reagent flow through the dispense port.

6. The immunoassay apparatus of claim 1, further comprising a second one-way valve coupled to the dispense port and configured to control the reagent flow through the dispense port.

7. The immunoassay apparatus of claim 1, further comprising a reagent storage chamber coupled to the reagent dispense chamber.

8. The immunoassay apparatus of claim 7, wherein the inlet port connects the reagent storage chamber and the reagent dispense chamber.

9. The immunoassay apparatus of claim 1, wherein the dispenser support contains two or more dispenser apparatus, each dispenser apparatus having a dispense port exiting downward from a bottom surface of the dispenser apparatus.

10. The immunoassay apparatus of claim 1, the moveable wall comprises a flexible diaphragm.

11. A method of dispensing a reagent, comprising:

providing a reagent dispenser apparatus having a dispense port, an inlet port, a moveable wall, and a first one-way valve, the inlet port vertically offset from the dispense port, and the first one-way valve adapted and operable to control reagent flow through the inlet port;

providing an actuator coupled to an actuation member, the actuator operable to move the actuation member in a vertical direction;

moving the reagent dispense apparatus to a location where the actuation member is located beneath the vertically movable wall; and activating the actuator to move the actuation member upward to move the moveable wall of the reagent dispenser apparatus upward to accomplish dispensing of the reagent downward from the dispensing port, wherein dispensing the reagent from the reagent dispenser apparatus is accomplished without using a pipette or probe aspiration.

* * * * *